United States Patent
Strawbridge (12)

(10) Patent No.: US 6,978,792 B1
(45) Date of Patent: Dec. 27, 2005

(54) PUMP AND CONDUIT STERILIZING SYSTEM

(76) Inventor: Joseph M. Strawbridge, 703 Castlewood Dr., Upper Marlboro, MD (US) 20774

( * ) Notice: Subject to any disclaimer, the term of this patent is extended or adjusted under 35 U.S.C. 154(b) by 488 days.

(21) Appl. No.: 10/330,980

(22) Filed: Dec. 30, 2002

(51) Int. Cl.$^7$ ................................................ B08B 3/04
(52) U.S. Cl. .......................... 134/166 R; 134/169 R; 134/166 C; 4/490
(58) Field of Search ...................... 134/166 R, 169 R, 134/166 C; 4/490

(56) References Cited

U.S. PATENT DOCUMENTS

| | | | |
|---|---|---|---|
| 3,449,772 A | * | 6/1969 | Werner .......................... 4/490 |
| 4,193,870 A | * | 3/1980 | Goodin ........................ 210/805 |
| 4,676,894 A | | 6/1987 | Diamond et al. |
| 4,856,125 A | * | 8/1989 | Dijkhuizen ................. 4/541.1 |
| 4,859,345 A | | 8/1989 | Inagaki |
| 4,995,123 A | * | 2/1991 | Kern .............................. 4/490 |
| 5,109,880 A | * | 5/1992 | Booth .......................... 134/108 |
| D349,949 S | | 8/1994 | Formgren et al. |
| 5,381,566 A | | 1/1995 | Sonesson et al. |
| 5,545,335 A | | 8/1996 | Sween et al. |
| 5,682,628 A | | 11/1997 | Oleson |
| 5,694,957 A | * | 12/1997 | Lee, Jr. ................... 134/169 C |

FOREIGN PATENT DOCUMENTS

| | | | |
|---|---|---|---|
| DE | 34 30 714 | * | 12/1985 |
| DE | 38 26 001 | * | 2/1990 |
| DE | 41 08 539 | * | 9/1992 |

* cited by examiner

*Primary Examiner*—Frankie L. Stinson

(57) ABSTRACT

A pump and conduit sterilizing system for cleaning out and sterilizing the pump and the conduits attached to the pump for spas and swimming pools and the like. The pump and conduit sterilizing system includes a pliable spigot fitting member being adapted to attach to a spigot for a spa and a swimming pool; and also includes an intake hose being connected to the pliable spigot fitting member; and further includes an intake jet fitting member being adapted to attach to a selected liquid-forced jet; and also includes a cleaning solution assembly being connected to the intake hose and including a reservoir being adapted to hold cleaning solution therein, and also including a tubular member being attached to the reservoir and to the intake hose; and further includes a jet drainage assembly including a plurality of outtake jet fitting members being adapted to be attached to selected liquid-forced jets, and also including outtake hoses being attached to the outtake jet fitting members, and further including a drainage manifold being attached to the outtake hoses; and further including one or more jet plug members being adapted to be removably attached about selected liquid-forced jets.

12 Claims, 6 Drawing Sheets

PUMP AND CONDUIT STERILIZING SYSTEM

BACKGROUND OF THE INVENTION

1. Field of the Invention

The present invention relates to pump and conduit sterilizing systems and more particularly pertains to a new pump and conduit sterilizing system for cleaning out and sterilizing the pump and the conduits attached to the pump for spas and swimming pools and the like.

2. Description of the Prior Art

The use of pump and conduit sterilizing systems is known in the prior art. More specifically, pump and conduit sterilizing systems heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,682,628; U.S. Pat. No. 5,545,335; U.S. Pat. No. 5,381,566; U.S. Pat. No. 4,859,345; U.S. Pat. No. 4,676,894; and U.S. Pat. No. Des. 349,949.

While these devices fulfill their respective, particular objectives and requirements, the aforementioned patents do not disclose a new pump and conduit sterilizing system. The prior art includes pipes, pumps and fittings for forcing water through the conduits and the pumps of the spas and/or swimming pools rather than using the system already provided.

SUMMARY OF THE INVENTION

The general purpose of the present invention, which will be described subsequently in greater detail, is to provide a new pump and conduit sterilizing system which has many of the advantages of the pump and conduit sterilizing systems mentioned heretofore and many novel features that result in a new pump and conduit sterilizing system which is not anticipated, rendered obvious, suggested, or even implied by any of the prior art pump and conduit sterilizing systems, either alone or in any combination thereof. The present invention includes a pliable spigot fitting member being adapted to attach to a spigot for a spa and a swimming pool; and also includes an intake hose being connected to the pliable spigot fitting member; and further includes an intake jet fitting member being adapted to attach to a selected liquid-forced jet; and also includes a cleaning solution assembly being connected to the intake hose and including a reservoir being adapted to hold cleaning solution therein, and also including a tubular member being attached to the reservoir and to the intake hose; and further includes a jet drainage assembly including a plurality of outtake jet fitting members being adapted to be attached to selected liquid-forced jets, and also including outtake hoses being attached to the outtake jet fitting members, and further including a drainage manifold being attached to the outtake hoses; and further including one or more jet plug members being adapted to be removably attached about selected liquid-forced jets. None of the prior art includes the combination of the elements of the present invention.

There has thus been outlined, rather broadly, the more important features of the pump and conduit sterilizing system in order that the detailed description thereof that follows may be better understood, and in order that the present contribution to the art may be better appreciated.

There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new pump and conduit sterilizing system which has many of the advantages of the pump and conduit sterilizing systems mentioned heretofore and many novel features that result in a new pump and conduit sterilizing system which is not anticipated, rendered obvious, suggested, or even implied by any of the prior art pump and conduit sterilizing systems, either alone or in any combination thereof.

Still another object of the present invention is to provide a new pump and conduit sterilizing system for cleaning out and sterilizing the pump and the conduits attached to the pump for spas and swimming pools and the like.

Still yet another object of the present invention is to provide a new pump and conduit sterilizing system that is easy and convenient to set up and use.

Even still another object of the present invention is to provide a new pump and conduit sterilizing system that prevents the backflow of cleaning solution into the spa and swimming pool.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
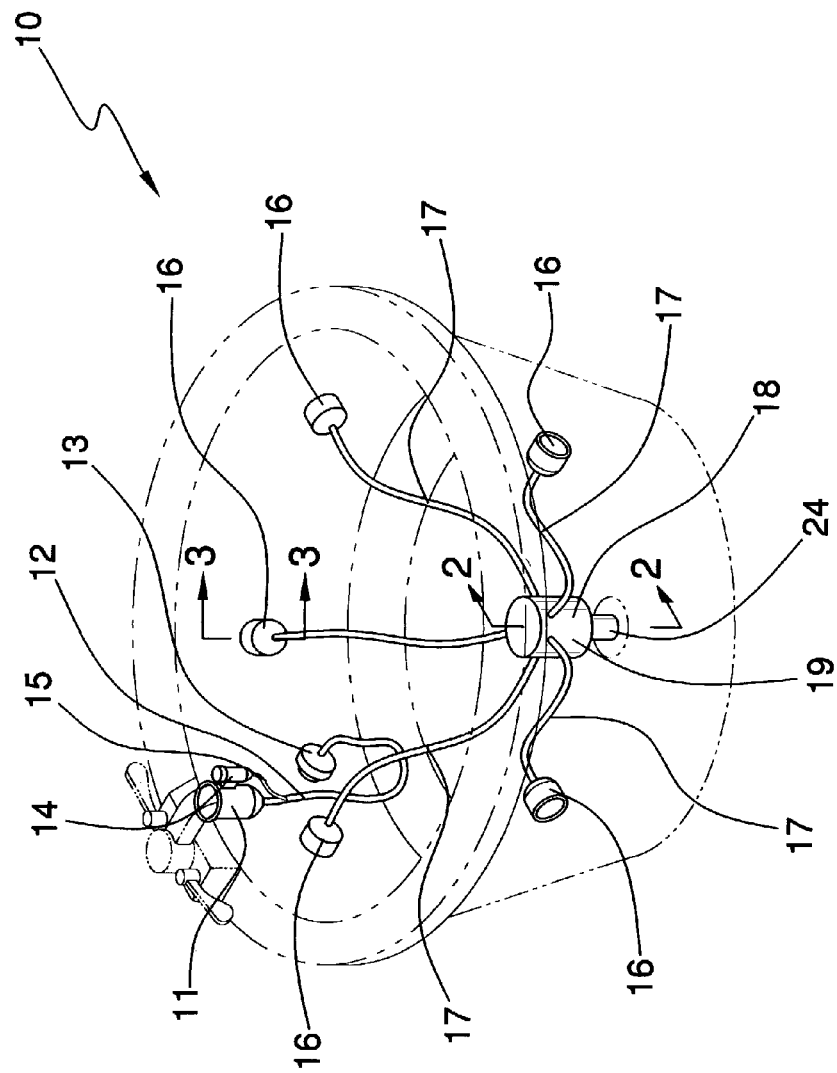
FIG. 1 is a perspective view of a new pump and conduit sterilizing system according to the present invention.
Figure 2:
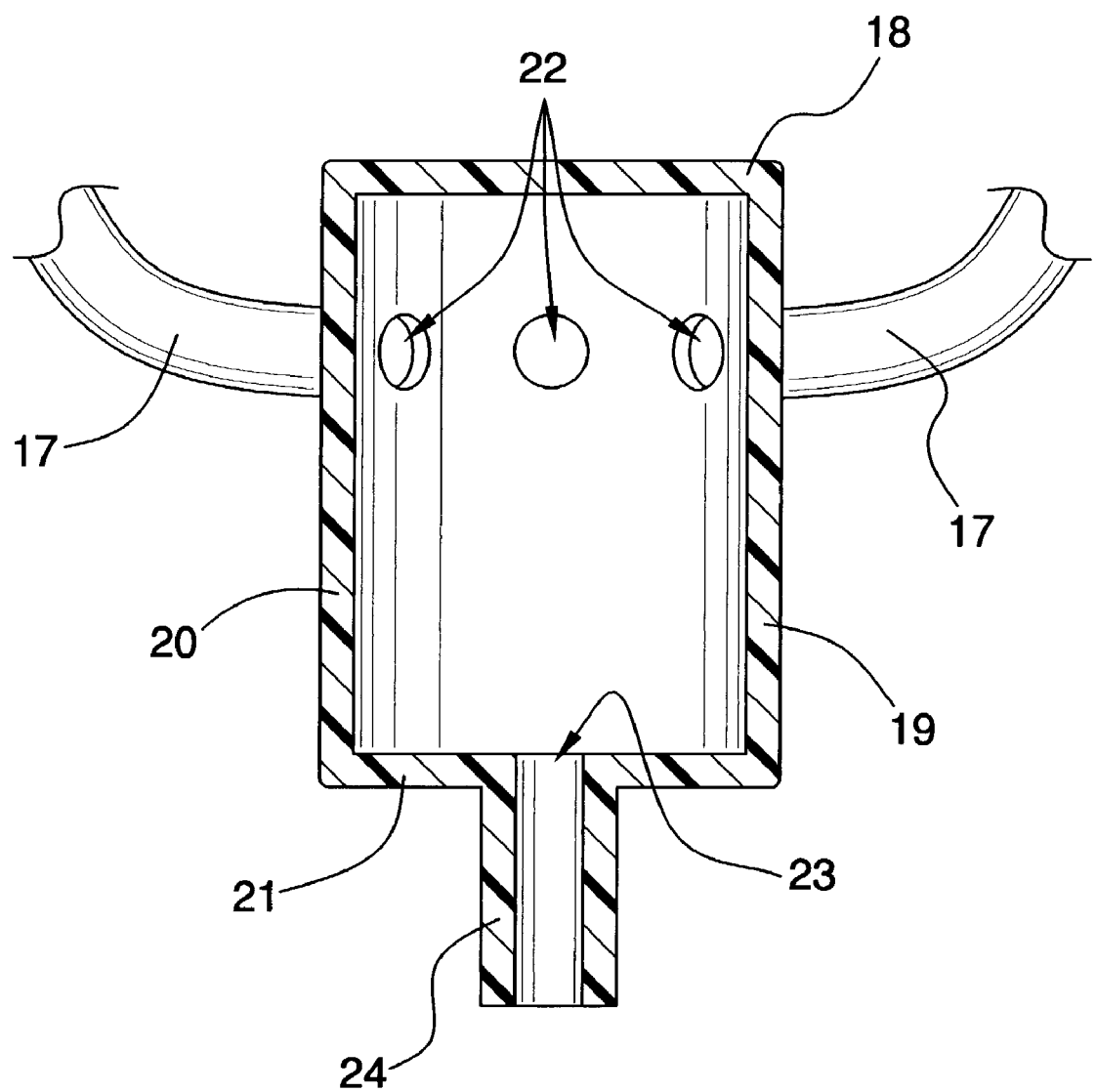
FIG. 2 is a cross-sectional view of the central drain fitting of the present invention.
Figure 3:
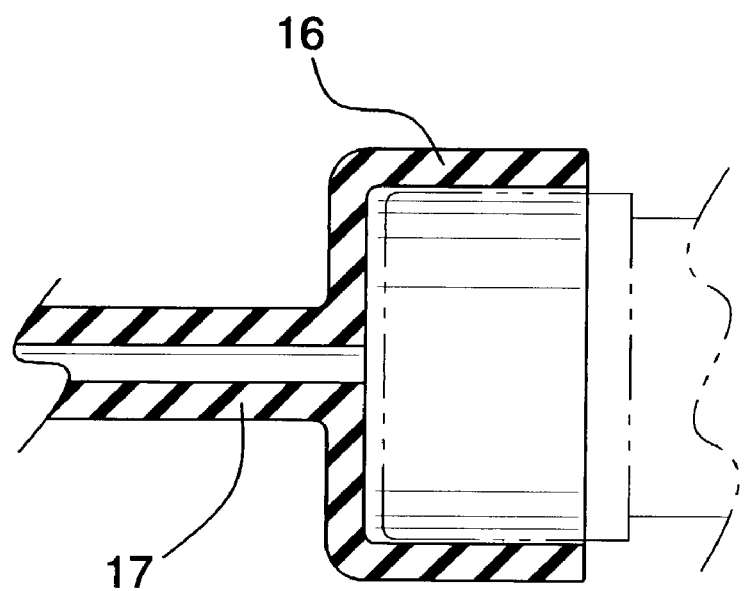
FIG. 3 is a cross-sectional view of one of the jet couplers of the present invention.
Figure 4:
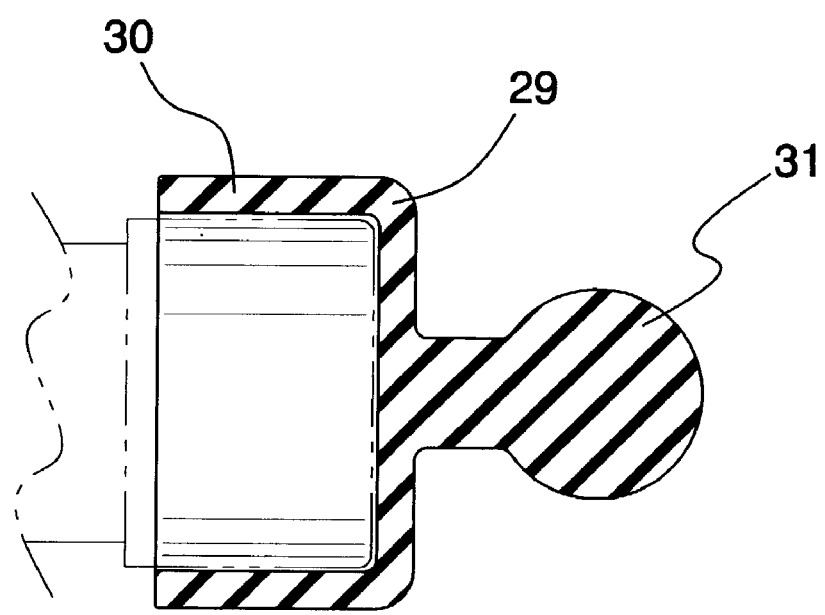
FIG. 4 is a cross-sectional view of one of the jet plug members of the present invention.
Figure 5:
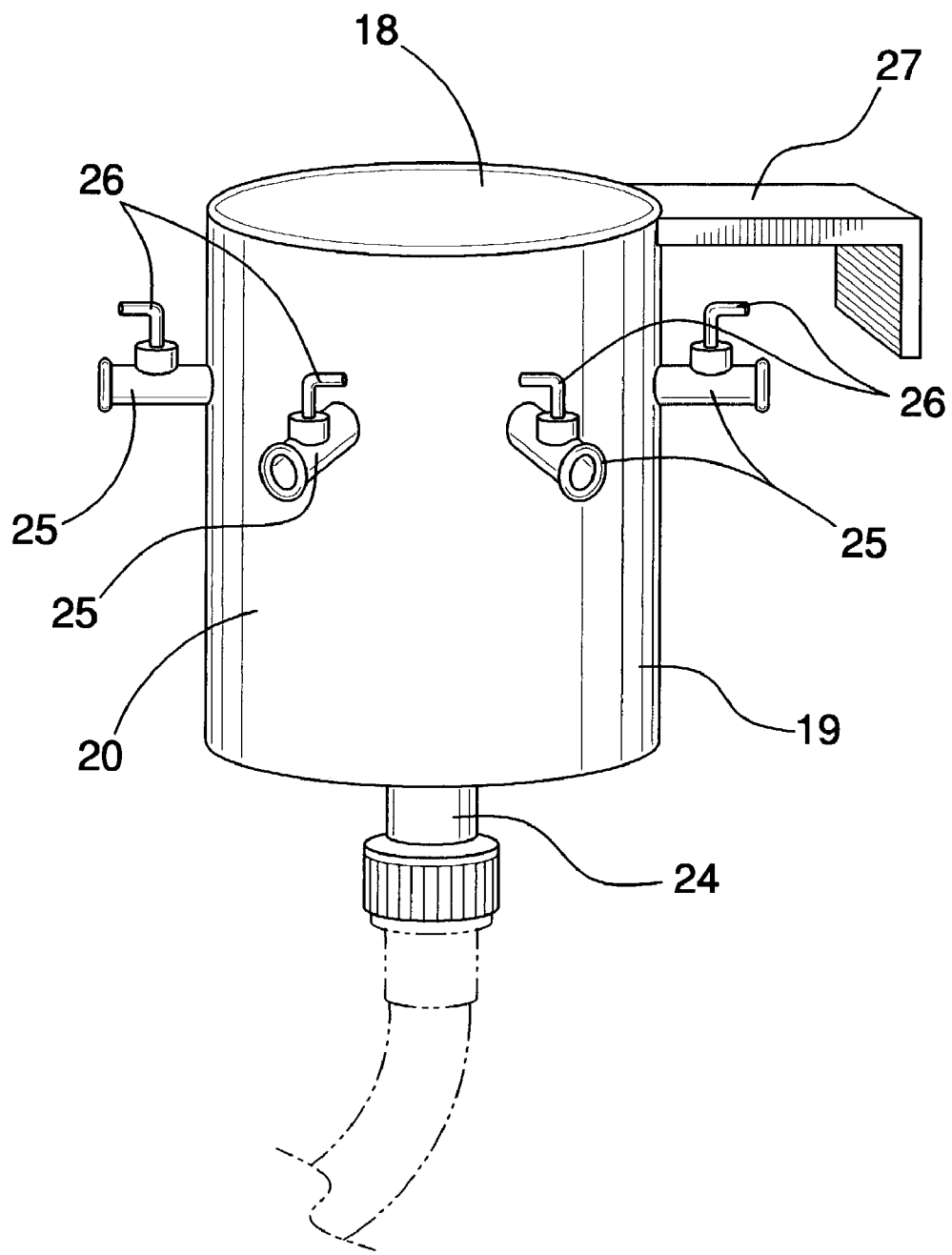
FIG. 5 is a perspective view of a second embodiment of the present invention.
Figure 6:
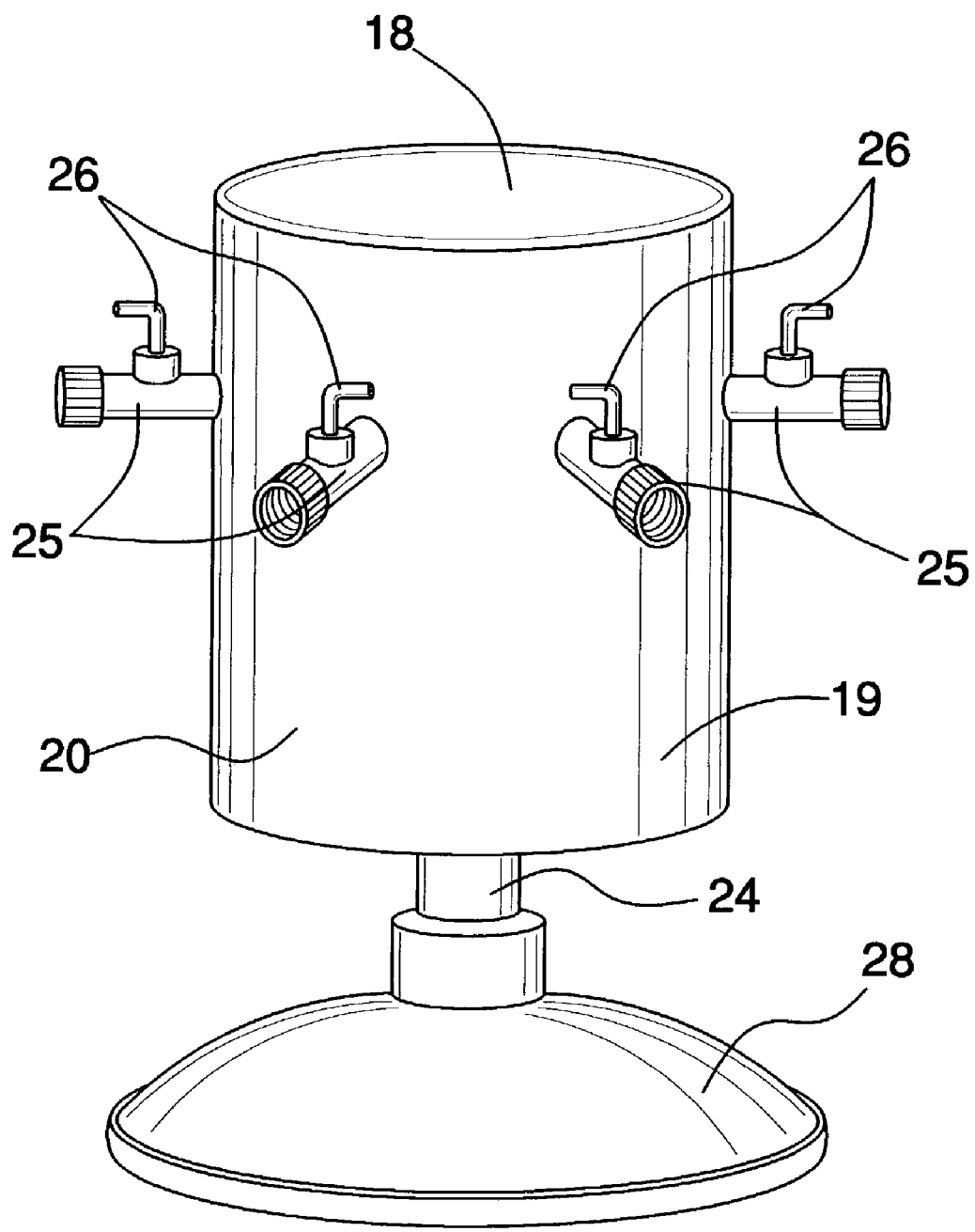
FIG. 6 is a perspective view of a third embodiment of the present invention.
Figure 7:
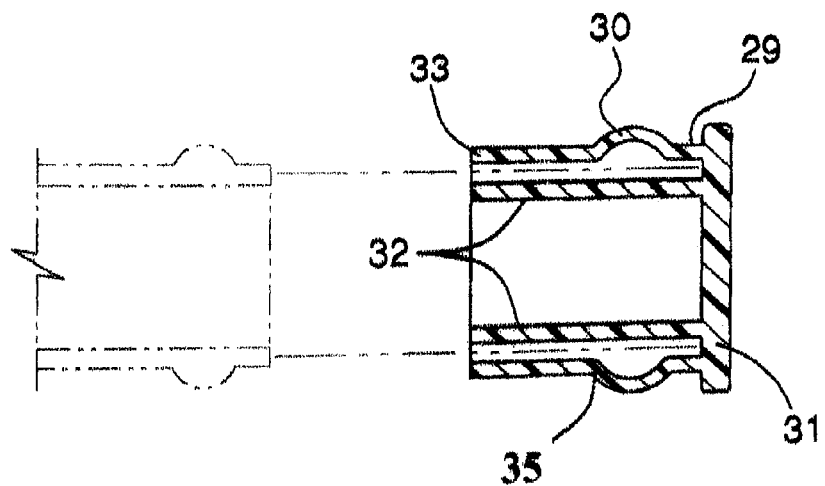
FIG. 7 is a cross-sectional view of a second embodiment of one of the jet plug members of the present invention.
Figure 8:
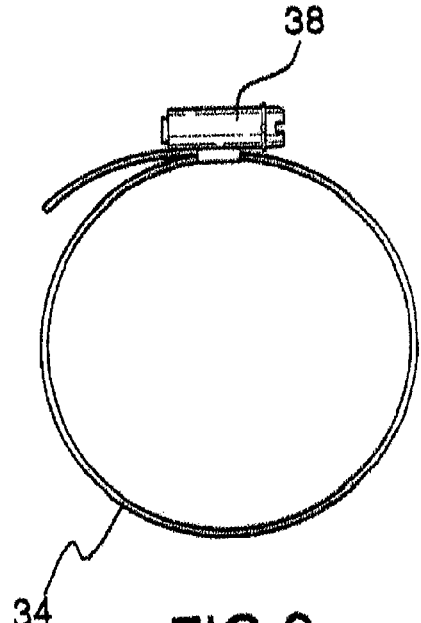
FIG. 8 is side elevational view of a fastener of the present invention.
Figure 9:
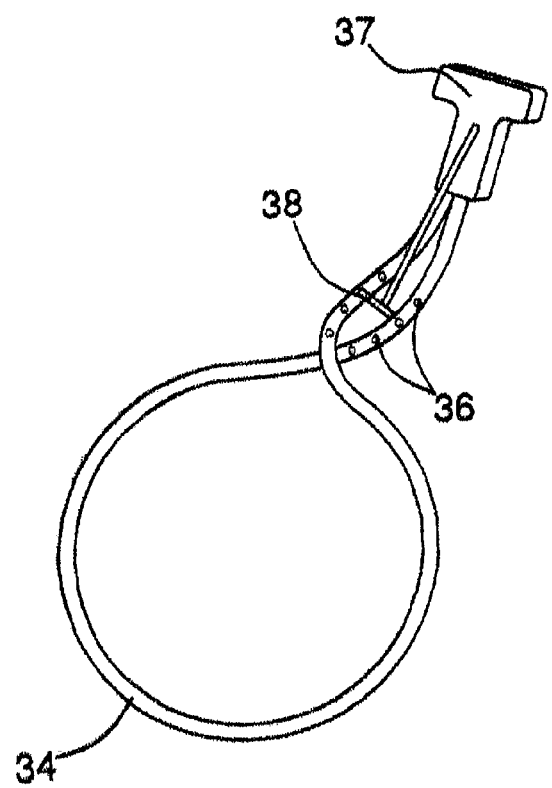
FIG. 9 is a side elevational view of another embodiment of a fastener of the present invention.

With reference now to the drawings, and in particular to FIGS. 1 through 9 thereof, a new pump and conduit sterilizing system embodying the principles and concepts of the present invention and generally designated by the reference numeral 10 will be described.

As best illustrated in FIGS. 1 through 9, the pump and conduit sterilizing system 10 generally comprises a pliable spigot fitting member 11 being adapted to attach to a spigot for a spa and/or a swimming pool. The pliable spigot fitting member 11 is generally a boot made of rubber material. An intake hose 12 is conventionally connected to the pliable spigot fitting member 11.

An intake jet fitting member 13 is adapted to be attached to a selected liquid-forced jet. A cleaning solution assembly is conventionally connected to the intake hose 12 and includes a reservoir 14 being adapted to hold cleaning solution therein, and also includes a tubular member 15 being conventionally attached to the reservoir 14 and to the intake hose 12 and having a bore being disposed therethrough.

A jet drainage assembly includes a plurality of outtake jet fitting members 16 being adapted to be attached to selected liquid-forced jets, and also includes outtake hoses 17 being conventionally attached to the outtake jet fitting members 16, and further includes a drainage manifold 18 being conventionally attached to the outtake hoses 17. The intake jet fitting member 13 and the outtake jet fitting members 16 are generally caps having perimeter walls for removably engaging about the selected liquid-forced jets. The drainage manifold 18 includes a container 19 having side and bottom walls 20, 21, and also having a plurality of holes 22 being spacedly disposed through the side wall 20, and further having a drainage opening 23 being disposed through the bottom wall 21. The drainage manifold 18 also includes a tubular drainage fitting 24 being conventionally attached over the drainage opening 23 and extending outwardly from the bottom wall 21 of the container 19 and being adapted to be removably engaged in a drain for the spa and swimming pool and having a bore being disposed therethrough. The outtake hoses 16 are securely and conventionally attached to the holes 22 of the container 19.

As a second embodiment, the drainage manifold 18 also includes a plurality of spigots 25 being conventionally attached over the holes 22 of the container 19 and extending outwardly therefrom, and further having valve members 26 being conventionally disposed in the spigots 25, and further includes a tubular drainage fitting 24 being conventionally attached over the drainage opening 23 and extending outwardly from the bottom wall 21 of the container 19 and being adapted to fasten to a drainage hose and having a bore being disposed therethrough. The outtake hoses 16 are conventionally attachable to the spigots 25. The drainage manifold 18 also includes a bracket 27 being conventionally attached to an outer side of the side wall 20 of the container 19 and being adapted to hang upon a side wall of the spa and the swimming pool.

As a third embodiment, the drainage manifold 18 also includes a suction cup member 28 being conventionally attached to an end of the tubular drainage fitting 24 and being adapted to being suctioned upon a wall of the spa and swimming pool.

One or more jet plug members 29 are adapted to be removably attached about selected liquid-forced jets. Each of the one or more jet plug members 29 includes a cap portion 30 being adapted to securely fit about a selected liquid-forced jet and having node portions conventionally protruding outwardly from a side wall of the cap portion 30 for locking the cap portion 30 about the selected liquid-forced jet, and also includes a handle portion 31 for manipulating the cap portion 30. Fasteners are fastenable about the jet plug members 29. Each fastener includes a tie member 34 having a plurality of holes 36 being disposed along a portion thereof and also includes a T-shaped handle member 37 being conventionally attached to the tie member 34 and further includes a tie-member locking member 38 for securing the tie member 38 about the respective jet plug member 29.

In use, the user turns on the spigot for the spa and/or swimming pool; whereupon, water passes through the intake hose 12 and draws in the cleaning solution from the reservoir 14 and passes the water with the cleaning solution through a selected liquid-forced jet. The cleaning mixture moves through the conduit and the pump and out of the other liquid-forced jets and into the drainage manifold 19 which directs the waste water to a drainage sight rather than back into the spa and/or swimming pool.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the pump and conduit sterilizing system. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A pump and conduit sterilizing system comprising:
   a pliable spigot fitting member being adapted to attach to a spigot for a spa and a swimming pool;
   an intake hose being connected to said pliable spigot fitting member;
   an intake jet fitting member being adapted to be attached to a selected liquid-forced jet;
   a cleaning solution assembly being connected to the intake hose and including a reservoir being adapted to hold cleaning solution therein, and also including a tubular member being attached to said reservoir and to said intake hose and having a bore being disposed therethrough;
   a jet drainage assembly including a plurality of outtake jet fitting members being adapted to be attached to selected liquid-forced jets, and also including outtake hoses being attached to the outtake jet fitting members, and further including a drainage manifold being attached to said outtake hoses; and
   one or more Jet plug members being adapted to be removably attached about selected liquid-forced jets.

2. The pump and conduit sterilizing system as described in claim 1, wherein said pliable spigot fitting member is generally a boot made of rubber material.

3. The pump and conduit sterilizing system as described in claim 2, wherein said intake jet fitting member and said outtake jet fitting members are generally caps having perimeter walls for removably engaging about the selected liquid-forced jets.

4. The pump and conduit sterilizing system as described in claim 3, wherein said drainage manifold includes a container having side and bottom walls, and also having a plurality of holes being spacedly disposed through said side wall, and further having a drainage opening being disposed through said bottom wall.

5. The pump and conduit sterilizing system as described in claim 4, wherein said drainage manifold also includes a tubular drainage fitting being attached over said drainage opening and extending outwardly from said bottom wall of said container and being adapted to be removably engaged in a drain for the spa and swimming pool and having a bore being disposed therethrough.

6. The pump and conduit sterilizing system as described in claim 5, wherein said outtake hoses are securely attached to said holes of said container.

7. The pump and conduit sterilizing system as described in claim 4, wherein said drainage manifold also includes a plurality of spigots being attached over said holes of said container and extending outwardly therefrom, and further having valve members being disposed in said spigots, and further includes a tubular drainage fitting being attached over said drainage opening and extending outwardly from said bottom wall of said container and being adapted to fasten to a drainage hose and having a bore being disposed therethrough, said outtake hoses being attachable to said spigots.

8. The pump and conduit sterilizing system as described in claim 7, wherein said drainage manifold also includes a bracket being attached to an outer side of said side wall of said container and being adapted to hang upon a side wall of the spa and the swimming pool.

9. The pump and conduit sterilizing system as described in claim 7, wherein said drainage manifold also includes a suction cup member being attached to an end of said tubular drainage fitting and being adapted to being suctioned upon a wall of the spa and swimming pool.

10. The pump and conduit sterilizing system as described in claim 4, wherein each of said one or more jet plug members includes a cap portion being adapted to securely fit about a selected liquid-forced jet and also includes a handle portion.

11. The pump and conduit sterilizing system as described in claim 10, wherein said cap portion has node portions protruding outwardly from said side wall thereof for locking said cap portion about a selected said liquid-forced jet.

12. The pump and conduit sterilizing system as described in claim 10, wherein fasteners are fastenable about said jet plug members, each fastener including a tie member having a plurality of holes being disposed along a portion thereof and also including a T-shaped handle member being attached to said tie member and further including a tie-member locking member for securing said tie member about a respective said jet plug member.

* * * * *